(12) United States Patent
Kao et al.

(10) Patent No.: US 8,023,721 B2
(45) Date of Patent: Sep. 20, 2011

(54) PANEL INSPECTION DEVICE AND INSPECTION METHOD OF PANEL

(75) Inventors: Hsien-Chang Kao, Taoyuan County (TW); Ching-Chun Chien, Taoyuan County (TW); Chih-Chiang Lee, Taoyuan (TW); Kuo-Chang Teng, Taoyuan County (TW)

(73) Assignee: Chunghwa Picture Tubes, Ltd., Bade, Taoyuan (TW)

( * ) Notice: Subject to any disclaimer, the term of this patent is extended or adjusted under 35 U.S.C. 154(b) by 414 days.

(21) Appl. No.: 12/425,396

(22) Filed: Apr. 17, 2009

(65) Prior Publication Data

US 2010/0040277 A1  Feb. 18, 2010

(30) Foreign Application Priority Data

Aug. 18, 2008 (TW) ................ 97131406 A

(51) Int. Cl.
*G06K 9/00* (2006.01)
(52) U.S. Cl. ...................................... 382/141
(58) Field of Classification Search .......... 349/187, 349/192; 382/141, 152, 144
See application file for complete search history.

(56) References Cited

U.S. PATENT DOCUMENTS

| | | | |
|---|---|---|---|
| 6,924,657 B2* | 8/2005 | Kamieniecki et al. | 324/754.03 |
| 7,079,216 B2* | 7/2006 | Yamazaki et al. | 349/158 |
| 7,295,279 B2* | 11/2007 | Byun et al. | 349/187 |
| 7,356,176 B2* | 4/2008 | Fujii et al. | 382/141 |
| 7,372,527 B2* | 5/2008 | Kawase | 349/106 |
| 7,778,458 B2* | 8/2010 | Hiraoka | 382/141 |
| 7,806,251 B2* | 10/2010 | Noda et al. | 198/601 |
| 7,830,502 B2* | 11/2010 | Iwai et al. | 356/237.5 |
| 2009/0028419 A1* | 1/2009 | Yokono et al. | 382/141 |
| 2010/0141754 A1* | 6/2010 | Hiraoka | 348/93 |
| 2010/0142796 A1* | 6/2010 | Chang et al. | 382/141 |
| 2010/0145504 A1* | 6/2010 | Redford et al. | 700/227 |
| 2010/0214632 A1* | 8/2010 | Ikari et al. | 358/475 |
| 2010/0236903 A1* | 9/2010 | Noda et al. | 198/890 |
| 2010/0238442 A1* | 9/2010 | Heng et al. | 356/343 |
| 2010/0239124 A1* | 9/2010 | Hazeyama et al. | 382/103 |
| 2010/0284609 A1* | 11/2010 | Ding et al. | 382/154 |
| 2010/0322473 A1* | 12/2010 | Taylor et al. | 382/103 |
| 2011/0052039 A1* | 3/2011 | Urabe et al. | 382/141 |
| 2011/0164805 A1* | 7/2011 | Blair et al. | 382/137 |

FOREIGN PATENT DOCUMENTS

| | | |
|---|---|---|
| TW | 492540 | 6/2002 |
| TW | M285884 | 1/2006 |
| TW | M287936 | 2/2006 |
| TW | I273233 | 2/2007 |

* cited by examiner

*Primary Examiner* — Michael A Lyons
*Assistant Examiner* — Scott Richey
(74) *Attorney, Agent, or Firm* — Winston Hsu; Scott Margo

(57) ABSTRACT

A panel inspection device and inspection method is provided. At least an image capturing element is disposed above or below a spacing between a first conveyer and a second conveyer. During a panel is conveyed from the first conveyer to the second conveyer, the image capturing element captures the image of the panel as the panel passes through the spacing.

25 Claims, 8 Drawing Sheets

PANEL INSPECTION DEVICE AND INSPECTION METHOD OF PANEL

BACKGROUND OF THE INVENTION

1. Field of the Invention

The present invention relates to a panel inspection device and a panel inspection method, and more particularly, to a panel inspection device and a panel inspection method by executing the inspection to the panel between two adjacent conveyers.

2. Description of the Prior Art

Compared with a traditional non-flat display panel, such as cathode ray tube display, a flat display panel has been a mainstream product in the market because of having the characteristics of lightweight and thin thickness. The types of flat display panel can be sorted into a plasma display, a liquid crystal (LC) display, and an organic light-emitting display (OLED) according to different display technologies. In order to maintain the quality of display products, every type of above-mentioned display panels has to be inspected during its fabrication process for eliminating products with defects. Taking the liquid crystal display panel as an example, after the formation of electric elements on the upper and lower glass substrates, the fabrication processes include spreading spacers, cell assembly, cell cut, LC-injection, and sealing. After the stage of cell cut, it is required to inspect if there is any defects on the edge of the glass substrates. On the other hands, in a mass production of panels with various sizes and specifications, a process in the production line includes to identify the characteristics (such as two-dimensional bar codes) on the various panel products for managing the fabrication process of panels. Therefore, it is an essential procedure to inspecting the surface of panel in production line of a panel factory. The conventional inspection method of panel surface is performed by visual inspecting. In order to improve the efficiency and accuracy of inspection, the manufacturers have provided inspection equipment with automation functionality.

However, current inspection equipment includes many mechanism apparatuses and has to be operated with complicated process, which influences the total tact time of production. A Taiwan patent No. TW I273233 discloses a panel inspection device includes at least two linear guiders perpendicular with each other, a rotator, a carrier, a rotation motor, four scanners, and two positioning apparatuses. The carrier is used for carrying the panel to be inspected by vacuum fastening for instance. During the inspection process, the panel has to be positioned at first and then be fixed on the carrier. After that, the scanners are enabled to move to appropriate locations along a linear guider, and then the panel is moved by the carrier along another linear guider in order to be inspected. After the scanners inspect the two long sides or two short sides of the panel, enable the rotator to rotate the carrier so that the panel is rotated with an angle of 90 degrees, and than enable the panel to shift along the linear guider so that the scanners can inspect the other two side rims. After the inspection, a process of breaking vacuum is carried out, and a claw is used for taking the panel from the carrier. Accordingly, the process of the prior-art inspection method of panel is very complicated, and the steps of clawing and fastening the panel easily scratch or damage the panel. In addition, the common panel inspection device used by the manufacturers includes many mechanism apparatuses and occupies a certain equipment space that costs lots of money for maintaining and spare parts.

SUMMARY OF THE INVENTION

It is an object of the present invention to provide an inspection method of panels and a panel inspection device that utilizes a spacing between two adjacent panel conveyers to perform the inspection process, so as to solve the above-mentioned problem that the conventional inspection equipment is too bulky and the conventional inspection process is too complex.

According to the claimed invention, a panel inspection device for inspecting a panel is provided, wherein the panel has at least a first side rim and least a second side rim. The panel inspection device comprises a first image capturing element disposed above or below a spacing between a first conveyer and a second conveyer, wherein the first conveyer is used for transferring the panel to the second conveyer along a direction substantially parallel to the first side rim; a datum sensor disposed in the spacing or on the first conveyer; and a first linear delivering mechanism disposed above or below the spacing, substantially along the direction of the spacing and corresponding to the first image capturing element so that the first image capturing element is capable of executing a linearly-shifting movement above or below the spacing along the first linear delivering mechanism. When the second side rim of the panel passes through the datum sensor, the datum sensor will start the first image capturing element to execute an image-capturing motion to the panel after a predetermined time of the second side rim passes the datum sensor.

According to the claimed invention, an inspection method of panels is further provided. The inspection method is used for inspecting a panel that has at least a first side rim and at least a second side rim. The inspection method of panels comprises providing a first conveyer and a second conveyer adjacent to the first conveyer, wherein a spacing is positioned between the first conveyer and the second conveyer, and the first conveyer is used for transporting the panel to the second conveyer along a direction parallel to the first side rim; and providing a panel inspection device that comprises a first image capturing element disposed above or below the spacing and a datum sensor disposed in the spacing or on the first conveyer. During inspecting the panel, the first conveyer is utilized to transporting the panel to the second conveyer. When the second side rim of the panel passes through the datum sensor, the first image capturing element is enabled to execute an image-capturing motion to the panel after a pre-determined time.

It is an advantage of the present invention that the spacing between the adjacent conveyers is utilized to perform the panel inspection, so that only an image capturing element, a datum sensor, and a linear delivering mechanism are needed for performing the inspection of at least a surface of the panel, which is being transported, in the spacing. Therefore, the panel inspection device of the present invention only needs a few mechanisms or apparatus, and the inspection process is simplified in contrast to the prior art, so as to save the cost of equipments and increase the manufacturing efficiency.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
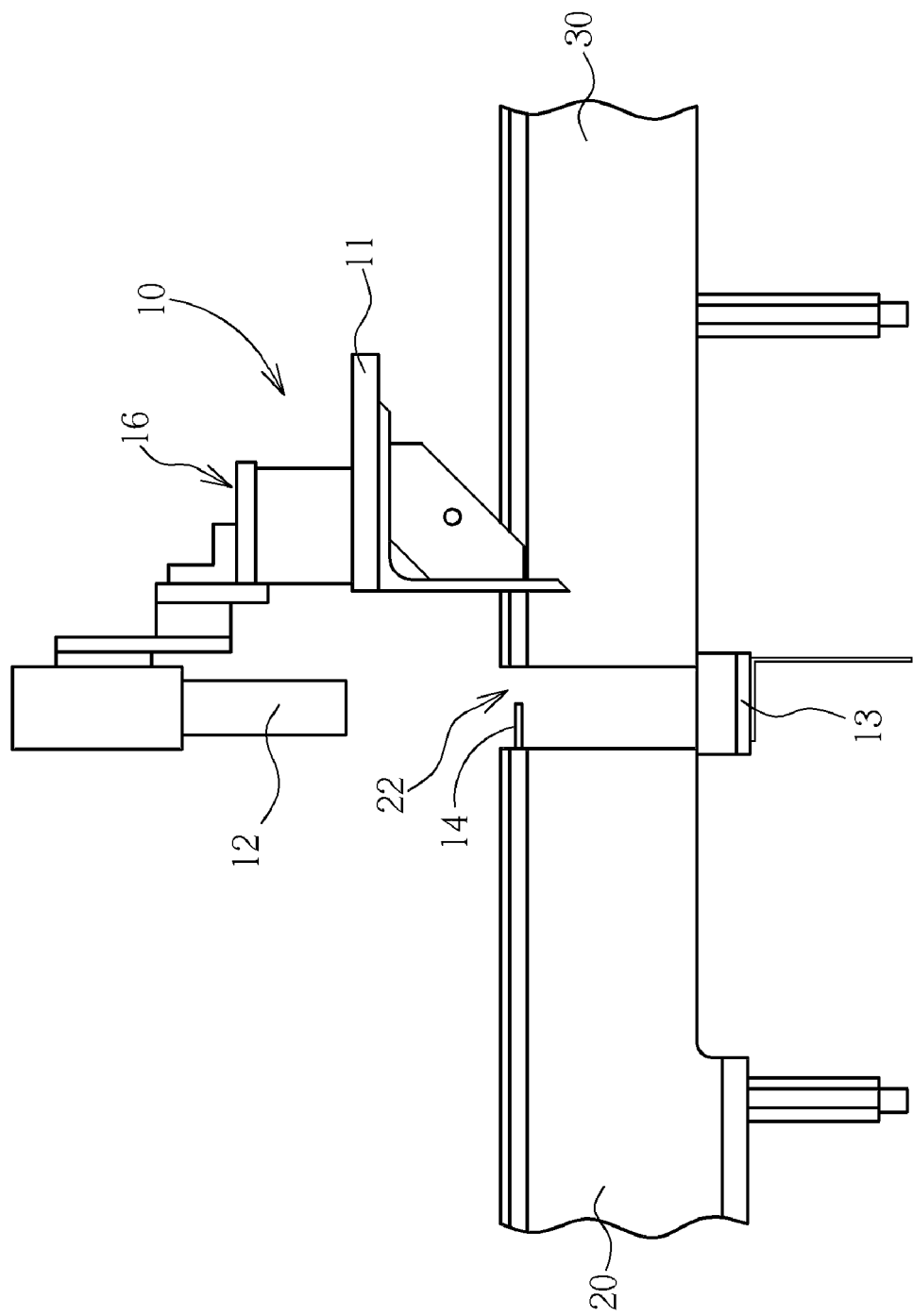
FIG. 1 is a schematic diagram of side appearance of a panel inspection device according to a first embodiment of the present invention.
Figure 2:
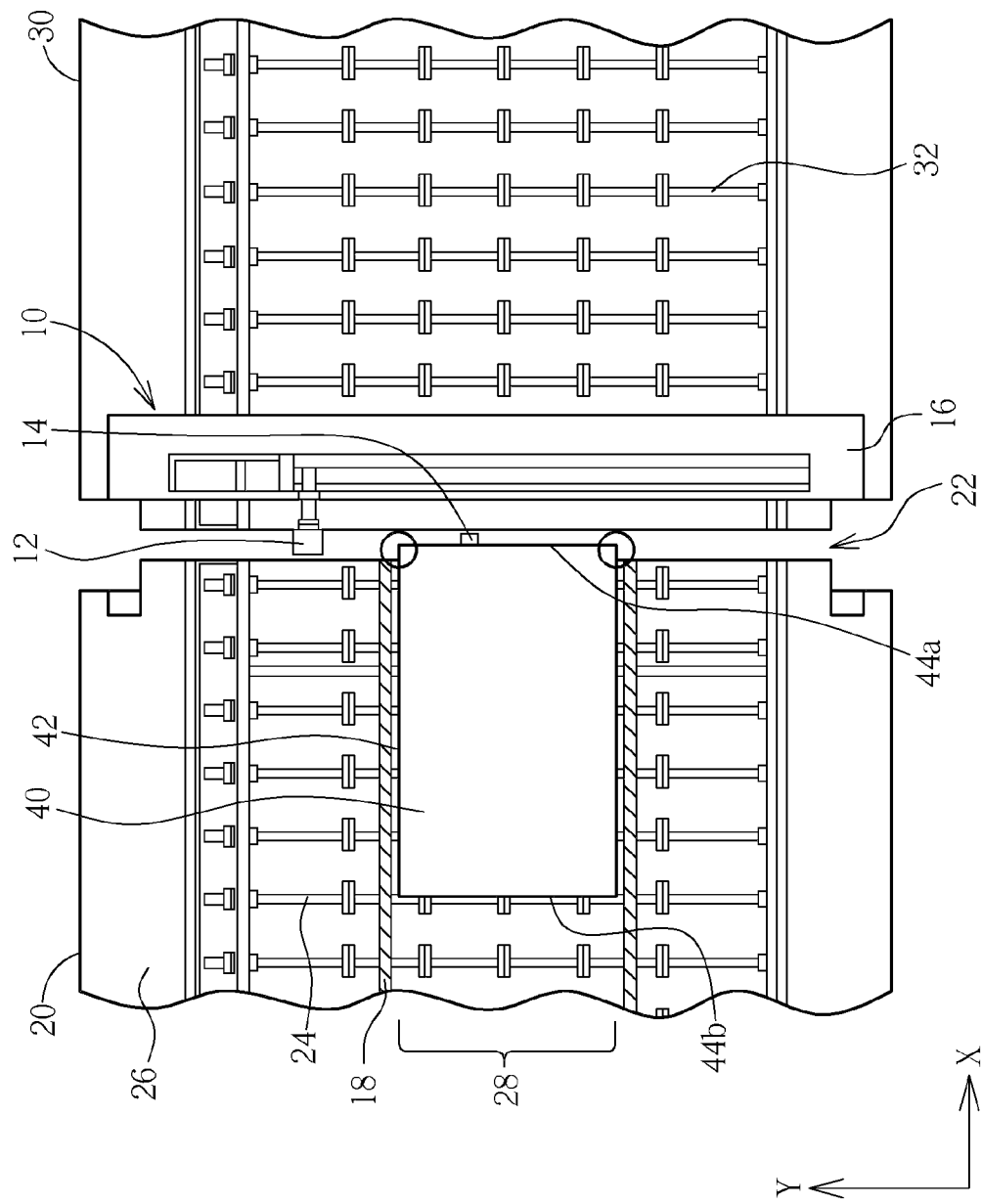
FIG. 2 is a schematic diagram of top appearance of the panel inspection device shown in FIG. 1.

Please refer to FIG. 1 to FIG. 2, wherein FIG. 1 is a schematic diagram of side appearance of a panel inspection device according to a first embodiment of the present invention, and FIG. 2 is a schematic diagram of top appearance of the panel inspection device shown in FIG. 1. The panel inspection device 10 of the present invention is substantially disposed between the adjacent first conveyer 20 and the second conveyer 30, wherein the first conveyer 20 and the second conveyer 30 are separate and individual transporting devices, and a spacing 22 is disposed between the first conveyer 20 and the second conveyer 30. The first conveyer 20 is capable of transporting the panel 40 to the second conveyer 30. In this embodiment, the panel 40 to be inspected has two first side rims 42 and two second side rims 44a, 44b. The second side rim 44a is positioned at the front edge of the transported panel 40, and the second side rim 44b is positioned at the back edge of the panel 40. In addition, in this embodiment, the first side rims 42 are the long sides of the rectangular panel 40, and the second side rims 44a, 44b are the short sides of the panel 40. The first conveyer 20 and the second conveyer 30 respectively have a plurality of rollers 24, 32, and may respectively have one or more transparent or opaque conveyer band (not shown) disposed above the rollers 24, 32. As the rollers 24, 32 keep on rolling, the first conveyer 20 and the second conveyer 30 transport the panel 40 substantially along a direction parallel to the direction of the first side rim 42, as the X-direction shown in FIG. 2.

The panel inspection device 10 of the present invention comprises at least an image capturing element 12 disposed above the spacing 22, a datum sensor 14 disposed in the spacing 22, and a linear delivering mechanism 16 disposed above the spacing 22 along a direction parallel to the spacing 22, corresponding to the first image capturing element 12. The linear delivering mechanism 16 may comprise a linear motor (not shown). The image capturing element 12 is movably connected to the linear delivering mechanism 16, so that it is capable of executing a linearly-shifting movement along the linear delivering mechanism 16 above the spacing 22, which means the image capturing element 12 is capable of moving forward or backward along Y-direction shown in FIG. 2. In this embodiment, the datum sensor 14 is disposed in the spacing 22, and a fixing element disposed on the first conveyer 20 or the second conveyer 30 may be used to fix the datum sensor 14 in the spacing 22. The datum sensor 14 may comprise a photoelectric switch for sensing whether the panel 40 on the first conveyer 20 reaches a specific position or not. However, according to other embodiments of the present invention, the datum sensor 14 may be directly disposed on the first conveyer 20, such as on the platform 26 of the first conveyer 20, or be disposed between the rollers 24 when the conveyer band is transparent.

The image capturing element 12 may comprise a charge coupled device (CCD), a complementary metal oxide semiconductor (CMOS) sensor, or other types of image sensor. When a CCD is used as the sensor of the image capturing element 12, it may include a line scan CCD or an area CCD. The panel inspection device 10 may further comprise a light source 13 positioned near the spacing 22 in order to provide a light source for the image-capturing motion. The light source 13 may be an in-line source of the image capturing element 12 or a backlight that positioned below the spacing 22, as shown in FIG. 1. In addition, the panel inspection device 10 may comprise an image platform 11 mounted on two sides of the second conveyer 30, and the linear delivering mechanism 16 and the image capturing element 12 are both disposed on the image platform 11. However, in other embodiment, the image platform 11 may be mounted on two sides of the first conveyer 20 or mounted on the first conveyer 20.

Figure 3:
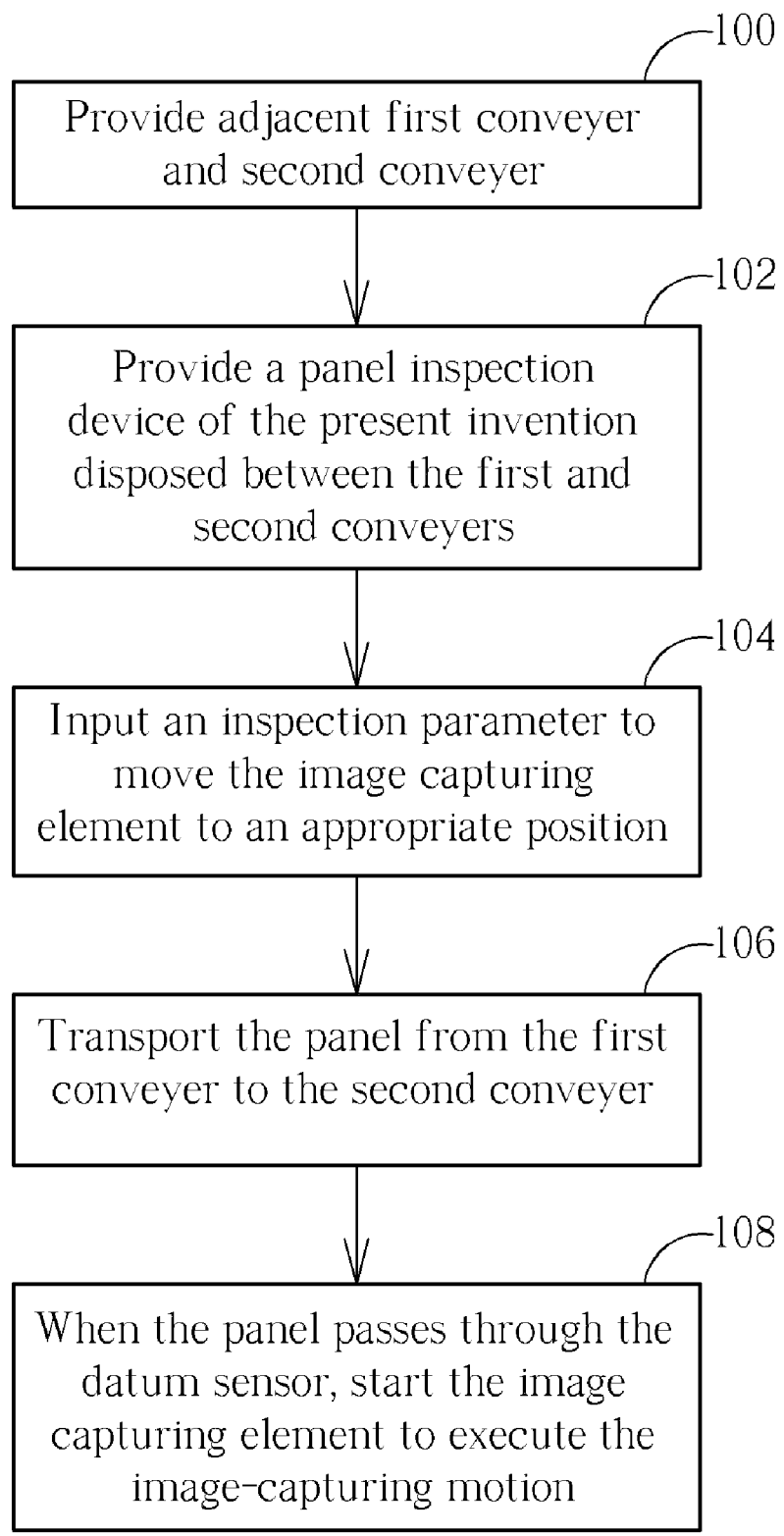
FIG. 3 is a process diagram of the panel inspection method according to a first embodiment of the present invention.

In the first embodiment of the present invention, the panel inspection device 10 may be used for inspecting a characteristic or a mark on the surface of the panel 40. For example, the characteristic or the mark may be located at a position which is circled as shown in FIG. 2. FIG. 3 shows the process of the inspection method to the characteristic or mark of the panel 40 according to the present invention by utilizing the panel inspection device 10, and the inspection method process comprises:

Step 100: Provide adjacent first conveyer 20 and second conveyer 30, wherein a spacing 22 is positioned between the first conveyer 20 and the second conveyer 30, and the first conveyer 20 may transport the panel 40 to the second conveyer 30 along a direction substantially parallel to the first side rim 42;

Step 102: Provide a panel inspection device 10 of the present invention disposed between the first conveyer 20 and the second conveyer 30, wherein the panel inspection device 10 comprises a first image capturing element 12 disposed above the spacing 22 between the first conveyer 20 and the second conveyer 30, a datum sensor 14 disposed in the spacing 22 and coupled to the first image capturing element 12, and a linear delivering mechanism 16 disposed above the spacing 22;

Step 104: Input an inspection parameter into the panel inspection device 10 according to the size, specification, and the location of the characteristic or mark of the panel 40 to be inspected, and enable the image capturing element 12 execute a linearly-shifting movement along the linear delivering mechanism 16 to an appropriate position so that the image capturing element 12 can directly capture the image of the characteristic or mark on the surface of the panel 40 without anymore shifting when the panel 40 passes through the spacing 22;

Step 106: Put the panel 40 on the first conveyer 20, and transport the panel 40 to the second conveyer 30 by the first conveyer 20 along the X-direction shown in FIG. 2, wherein the first conveyer 20 transports the panel 40 from the left side to the right side; and Step 108: Start the image capturing element 12 to execute an image-capturing motion to the panel 40 at a predetermined time after the second side rim 44a, the front edge, of the panel 40 (the right edge of the panel 40 in FIG. 2) passes through the datum sensor 14 according to the above-mentioned inspection parameter so as to capture the image of the characteristic or mark on the surface of the panel 40 for identifying.

The above-mentioned characteristic or mark of the panel 40 may include two-dimensional bar codes or other characteristics for identifying the specification of products or essential product characteristics during the fabrication. In addition, the panel inspection device 10 may further comprise a panel positioning mechanism 18 disposed on the first conveyer 20, used for transporting the panel 40 to the second conveyer 30 in a predetermined area 28 on the first conveyer 20. Accordingly, when the panel 40 passes through the spacing 22, the image capturing element 12 positioned on the linear delivering mechanism 16 does not have to linearly shift but can capture the image of the characteristic or mark on the panel 40 directly.

In other embodiments, the components of the present invention panel inspection device 10, such as image capturing element 12, datum sensor 14, or linear delivering mechanism 16, may alternatively be disposed below the spacing 22, while the light source 13 may be disposed above the spacing 22. In this situation, the process of the inspection method is similar to the above-mentioned steps for inspecting panels.

Figure 4:
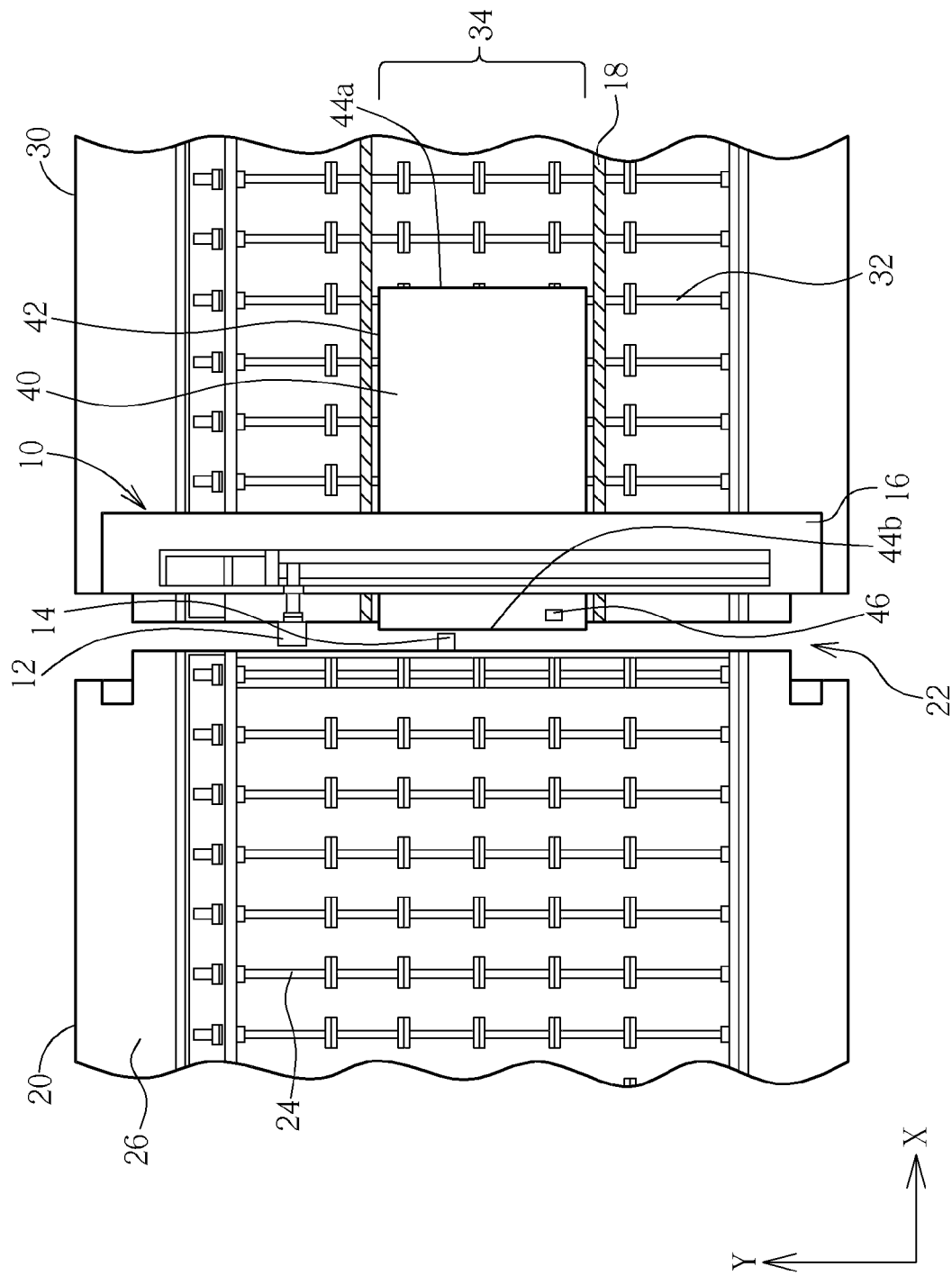
FIG. 4 is a schematic diagram of appearance of the facility of the panel inspection method according to another embodiment of the present invention.
Figure 5:
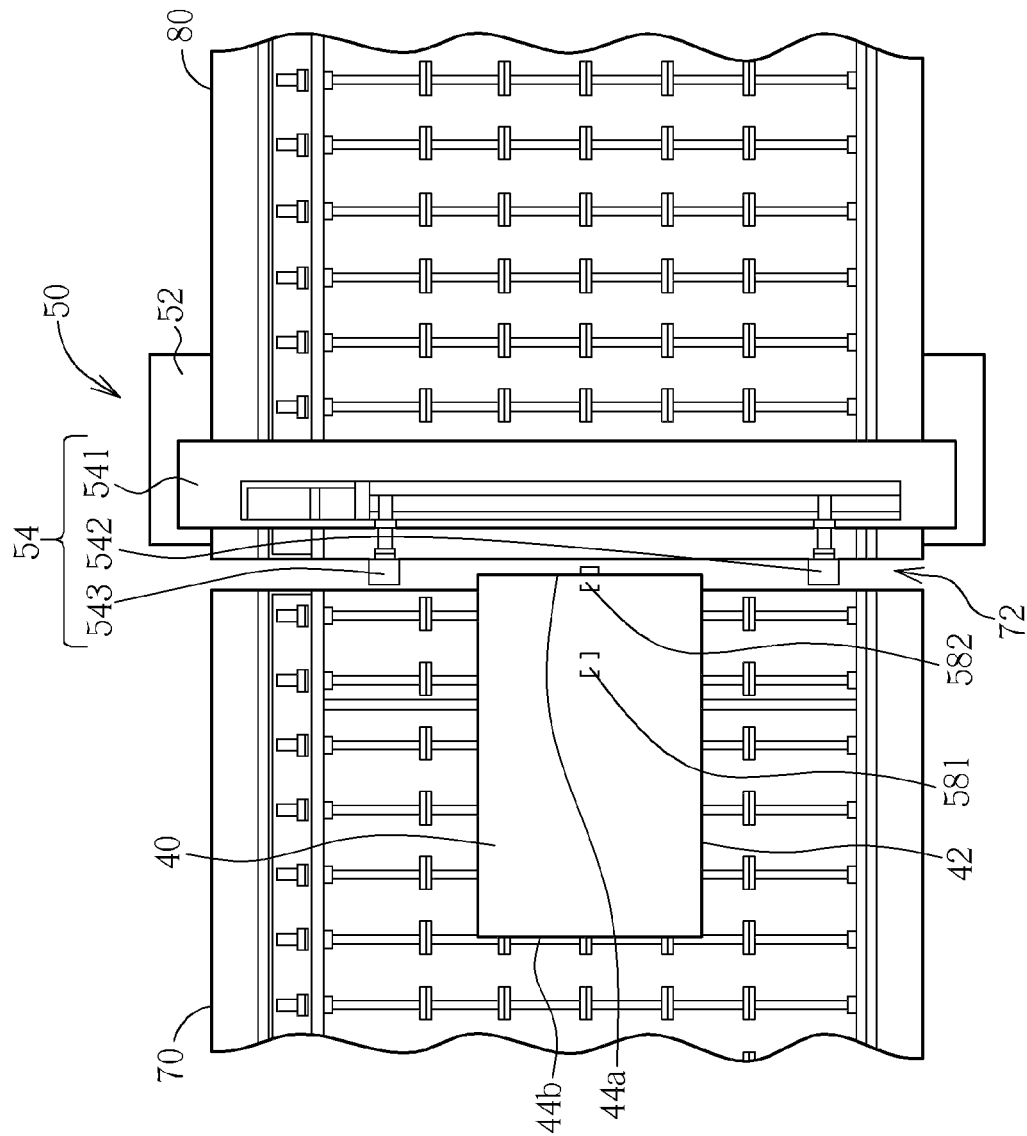
FIG. 5 is a schematic diagram of top appearance of the panel inspection device according to a second embodiment of the present invention.

Referring to FIG. 4, FIG. 4 is a schematic diagram of appearance of the facility of the panel inspection method according to another embodiment of the present invention. In this embodiment, the characteristic or mark (as the panel mark 46 shown in FIG. 4) of the panel 40 to be inspected is located near the back edge when the panel 40 is being transported. Accordingly, the inspection method of the present invention comprises setting various inspection parameters in the panel inspection device 10 to enable the image capturing element 12 to execute the image-capturing motion to a specific part near the second side rim 44b of the panel 40 passing through the spacing 22 at a longer time after the front edge of the panel 40, the second side rim 44a, passes through the datum sensor 14 such that the image capturing element 12 could just capture the image of the characteristic or mark disposed near the second side rim 44b. At this time, most part of the panel 40 has been transported on the second conveyer 30. Similarly, the panel inspection device 10 may further comprise a panel positioning mechanism 18 disposed on the second conveyer 30 so that the panel 40 is transported in a predetermined area 34 on the second conveyer 30. On the other side, the panel inspection method of the present invention may comprise inputting a setting to the panel inspection device 10 to enable the panel 40 to be moved backward with a predetermined distance and stopped after the second side rim 44b, the back edge of the panel 40, passes through the datum sensor 14 so that the panel mark 46 is stopped right in the spacing 22 and the image capturing element 12 can capture the image of the panel mark 46.

One of the advantages of the panel inspection method of the present invention is described as below. As the panel inspection such as identifying the characteristic of the panel 40 is performed, it is completed in the spacing 22 between the first and the second conveyer 20, 30 such that the transporting process of the panel 40 from the first conveyer 20 to the second conveyer 30 will not be affected at all. Therefore, the panel inspection and the transportation of the panel 40 by the first and the second conveyers 20, 30 may be performed at the same time. In addition, in other embodiments, the panel inspection 10 may be set to suspend the first or second conveyers 20, 30 from transporting the panel 40 for a short time or slow down the transportation speed (decelerate the panel) when the part of the panel 40 having the characteristic reaches the spacing 22 and to restore the transportation to a formal speed to keep on conveying the panel 40 to the second conveyer 30 after the image capturing element 12 captures the image of the characteristic. Accordingly, the present invention panel inspection device 10 and panel inspection method can effectively save the inspection time and raise the total production efficiency. Besides, the main components of the panel inspection device 10 may be disposed on the first or the second conveyers 20, 30 or mounted above the spacing 22 that also reduces the occupation space of equipments. Furthermore, since the panel inspection of the present invention is carried out in the spacing 22, it may utilize any kinds of light source for inspection because the light beams will not be blocked and the position of the light source can be adjusted according to specific requirements. For example, the light source 13 may be located under the spacing 22 to serve as a backlight to improve the performance f the image-capturing.

Figure 6:
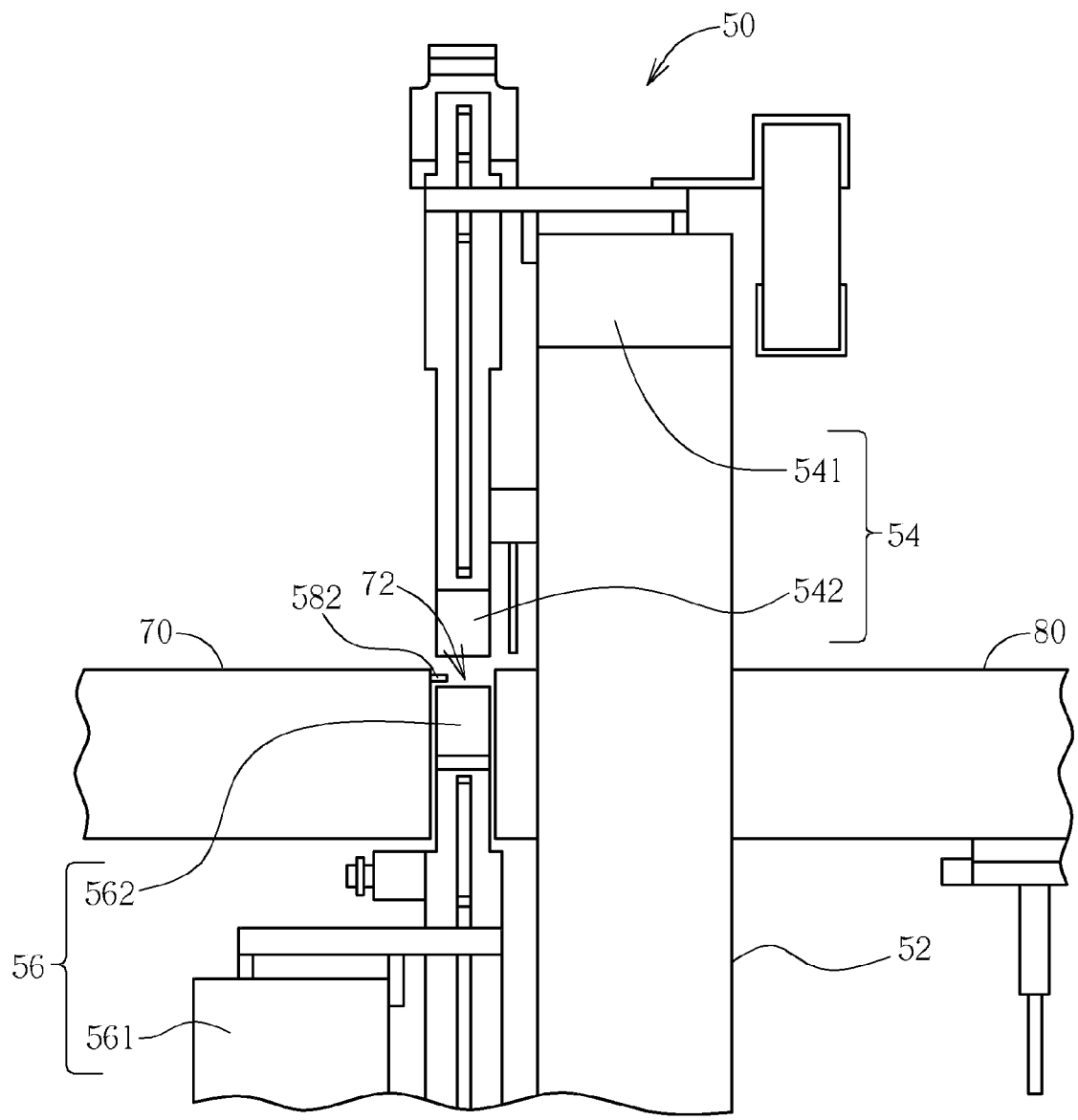
FIG. 6 is a schematic diagram of side appearance of the panel inspection device according to the second embodiment of the present invention.
Figure 7:
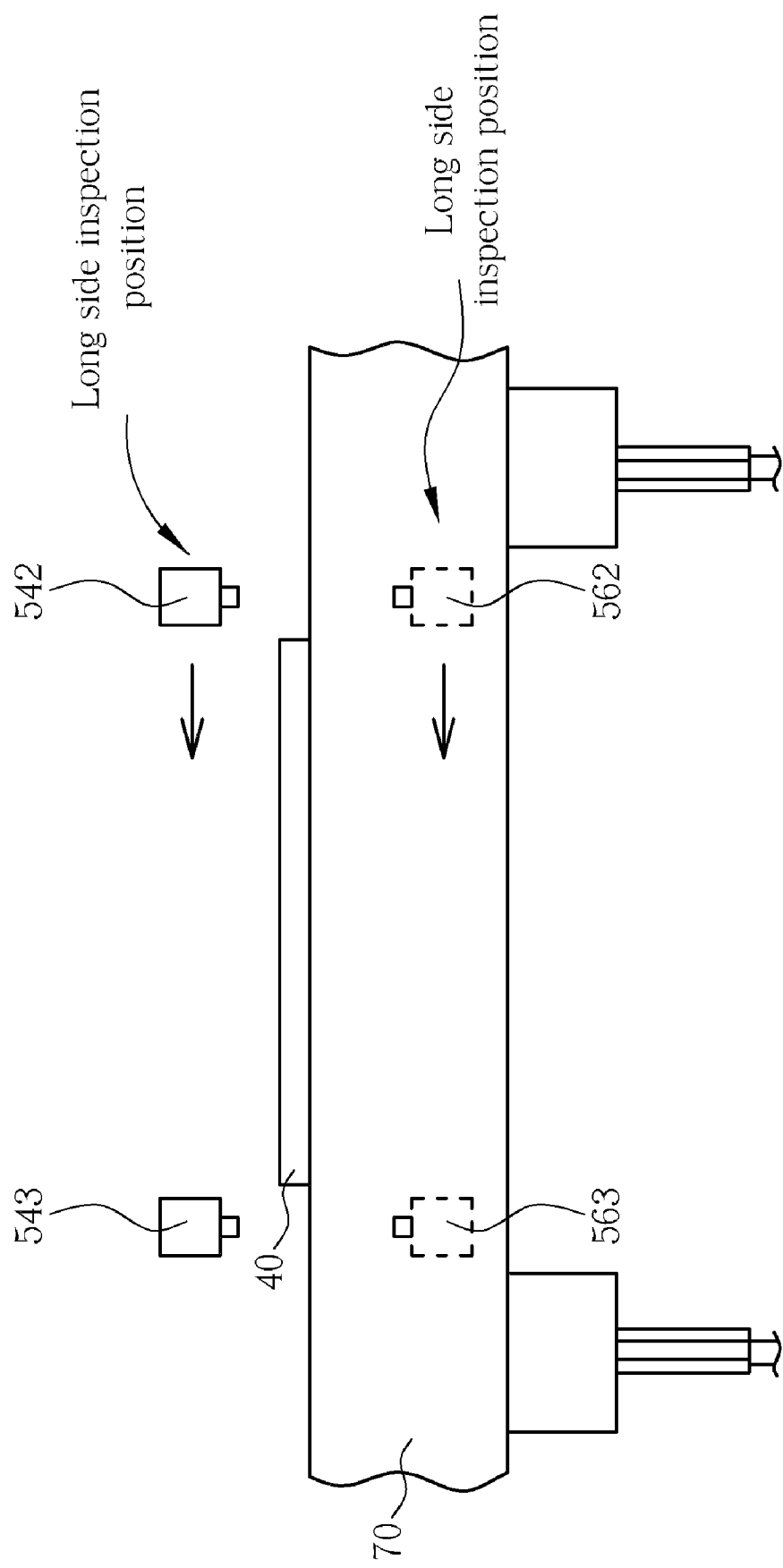
FIG. 7 is a schematic diagram of the movement route of the image capturing element of the panel inspection device according to the present invention.
Figure 8:
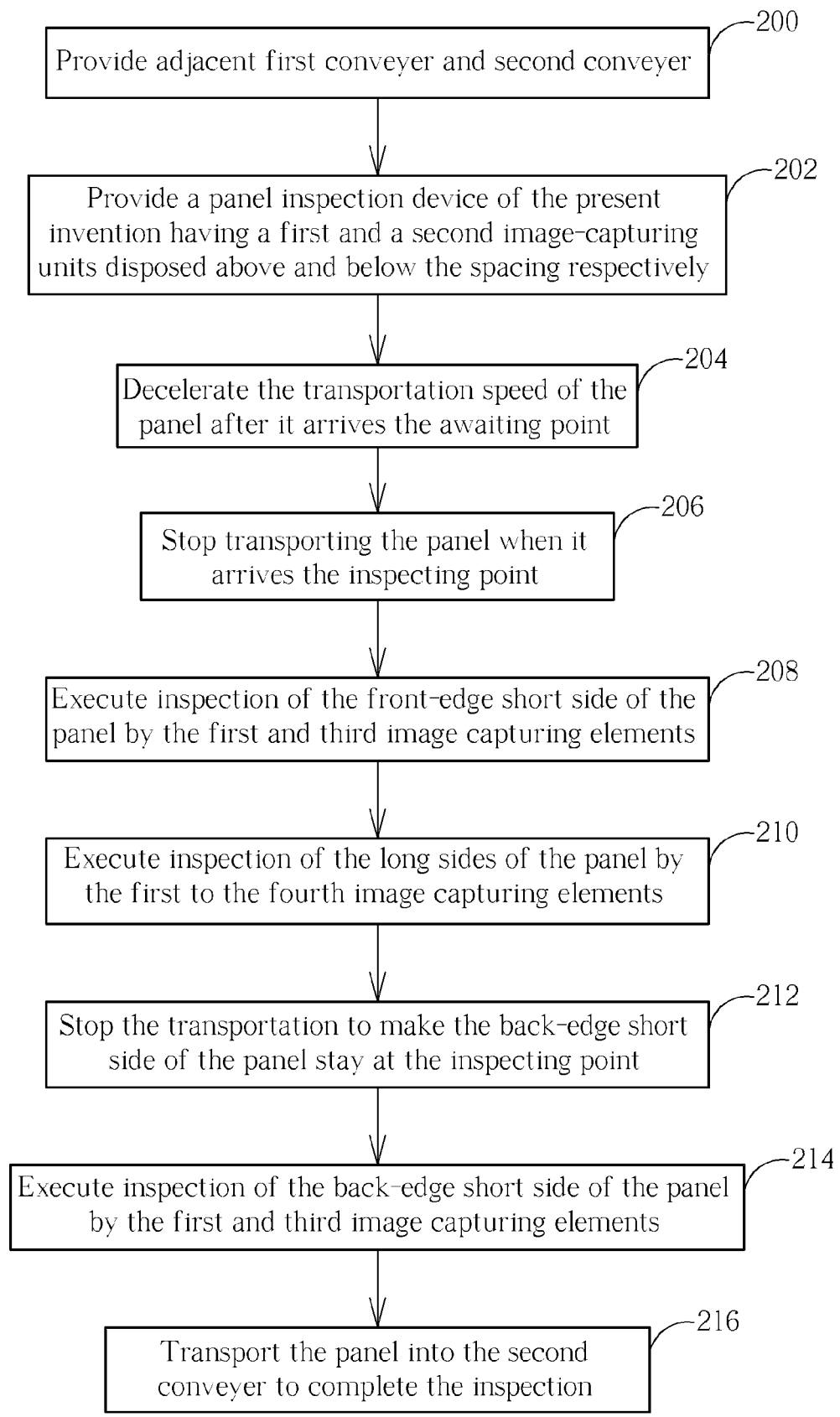
FIG. 8 is a process diagram of the panel inspection method according to the second embodiment of the present invention.

With reference to FIG. 5 to FIG. 8, FIG. 5 and FIG. 6 are schematic diagrams of top appearance and side appearance of the panel inspection device according to a second embodiment of the present invention respectively, FIG. 7 is a schematic diagram of the motion route of the image capturing element of the panel inspection device according to the present invention, and FIG. 8 is a process diagram of the panel inspection method according to the second embodiment of the present invention. In this embodiment, the panel inspection device 50 of the present invention may be used for inspecting the edge defects of the panel 40, which means it is used for inspecting if there is any defect on the upsides or downsides of the second side rim 44a, the second side rim 44b, and the first side rims 42 of the panel 40. The panel inspection device 50 is disposed near the spacing 72 between the two adjacent first conveyer 70 and second conveyer 80 and comprises an image platform 52 mounted at two sides of the second conveyer 80, a first image-capturing unit 54 disposed on the image platform 52, and a second image-capturing unit 56. The first image-capturing unit 54 comprises a first linear delivering mechanism 541, a first image capturing element 542, and a second image capturing element 543. Wherein, the first image capturing element 542 and the second image capturing element 543 are both located above the spacing 72. The first image capturing element 542 is movably connected onto the first linear delivering mechanism 541, and is capable of executing a linearly-shifting movement along the spacing 72 by leaning on a linear motor (not shown) included by the first linear delivering mechanism 541. During executing the linear-shifting movement, the first image capturing element 542 may execute continuous image-capturing motions to the top surface of the panel 40 passing through the spacing 72. In addition, the second image capturing element 543 may be directly fixed on the image platform 52 so as to be positioned above the spacing 72 for continuously capturing images. However, the second image capturing element 543 may also be movably connected to the first linear delivering mechanism 541 or other linear delivering mechanism so as to have the same function as the first image capturing element 542. For example, the second image capturing element 543 may linearly shift along the first linear delivering mechanism 541 and continuously capture the image of the panel 40 at the same time. The second image-capturing unit 56 comprises a third image capturing element 562, a fourth image capturing element 563 (shown in FIG. 7), and a second linear delivering mechanism 561 corresponding to the third image capturing element 562 and disposed under the spacing 72. FIG. 6 shows that the second linear delivering mechanism 561 is positioned below the first conveyer 70. The third image capturing element 562 is movably connected to the second linear delivering mechanism 561. The third image capturing element 562 may perform a linearly-shifting movement in the spacing 72 along the second linear delivering mechanism 561 by leaning on a leaner motor, and capture images of the panel 40 passing through the spacing 72 at the same time. The fourth image capturing element 563 is disposed at another side below the spacing 72, and may be fixed on the image platform 52 or be movably connected to the second linear delivering mechanism 561, similar to the third image capturing element 562, so that it can linearly shift along the spacing 72. Similar to the first embodiment, the spacing 72 is used as the inspecting point of the panel inspection device 50, and the first and the second image-capturing units 54, 56 may perform the inspection to the panel 40 passing through the spacing 72 at the same time.

In addition, the panel inspection device 50 may further comprise a first datum sensor 581 and a second datum sensor 582 disposed on the image platform 52 or the first conveyer 70. In this embodiment, the first and the second datum sensors 581, 582 are respectively disposed on the first conveyer 70 and in the spacing 72 for sensing if the panel 40 passes through a specific point of the first conveyer 70 or the spacing 72. The first datum sensor 581 is further coupled to the first conveyer 70 to control the transportation speed of the panel 40. For instance, according to the present invention, the location of the first datum sensor 581 may be determined as an awaiting point of the inspection process. When the panel 40 passes through the first datum sensor 581, the first conveyer 70 may slow down the transportation speed or stop transporting the panel 40 to keep the panel 40 stay at the awaiting point for a while, and then keep on transporting the panel 40 to pass the second datum sensor 582. On another side, the location of the second datum sensor 582 may be treated as an inspecting point of the panel 40, and the second datum sensor 582 may be coupled to the first and the second image-capturing units 54, 56. When the second datum sensor 582 senses the front edge of the panel 40, the second side rim 44a, is passing through, it may start the first and the second image-capturing units 54, 56 to perform image-capturing motions for inspecting the defects of the panel 40. Therefore, the first and the second datum sensors 581, 582 may also be coupled to the first and the second conveyers 70, 80 so as to control the first and the second conveyers 70, 80 to stop the transportation of the panel 40 or make the panel 40 to move forward or backward. Furthermore, the panel inspection device 50 may comprise a panel positioning mechanism (not shown), and the panel positioning mechanism is capable of performing a positioning process to the panel 40 when the panel 40 passes through the awaiting point in order to position the panel 40 in a predetermined area on the first conveyer 70 before it passes through the spacing 72 or before it is inspected.

The inspection method to the edge surface of the panel 40 by utilizing panel inspection device 50 according to the present invention may comprise the following steps, as shown in FIG. 8:

Step 200: Provide adjacent first conveyer 70 and second conveyer 80, wherein a spacing 72 is disposed between the first conveyer 70 and the second conveyer 80, and the first conveyer 70 is used for transporting the panel 40 to the second conveyer 80 substantially along a direction parallel to the first side rim 42;

Step 202: Provide the above-mentioned panel inspection device 50 of the present invention disposed between the first conveyer 70 and the second conveyer 80, wherein the panel inspection device 50 comprises a first image-capturing unit 54 disposed above the spacing 72 and a second image-capturing unit 56 disposed below the spacing 72 for inspecting a top surface and a bottom surface of the panel 40 respectively;

Step 204: Transport the panel 40 by the first conveyer 70, and slow down the transportation speed when the front edge of the panel 40, the second side rim 44a, passes through the first datum sensor 581, or decelerate the moving speed of the panel 40 when it passes through the awaiting point of the inspection process while a panel positioning mechanism may be used to positioning the location of the panel 40;

Step 206: When the front edge of the panel 40, the second side rim 44a, passes through the second datum sensor 582 or the awaiting point, the panel inspection device 50 suspends the first conveyer 70 from transporting the panel 40 so that the second side rim 44a is exposed in the spacing 72;

Step 208: Enable the first and the third image capturing elements 542, 562 to execute transversely linear-shifting movements along the first and the second linear delivering mechanisms 541, 561 or the spacing 72 simultaneously so as to execute continuous image-capturing motions to the top and bottom surfaces of the second side rim 44a, and after the above-mentioned inspection, enable the first and third image capturing elements 542, 562 to shift to a long side inspection position, which means the first and the second image capturing elements 542, 543 are positioned at two sides above the panel 40, while the third and fourth image capturing elements 562, 563 are located at two sides under the panel 40;

Step 210: Start the first conveyer 70 to keep on transporting the panel 40, and utilize the first, the second, the third, and the fourth image capturing elements 542, 543, 562, 563 to perform continuous image-capturing motions to both the upsides and downsides surfaces of the two first side rims 42 of the panel 40 that passes through the spacing 72 when the panel 40 is transported into the second conveyer 80; meanwhile, the first, the second, the third, and the fourth image capturing elements 542, 543, 562, 563 are all fixed without any moving;

Step 212: When the back edge of the panel 40, the second side rim 44b, leaves the second datum sensor 582, let the panel inspection device 50 control the first or the second conveyers 70, 80 to stop transporting the panel 40 so that the second side rim 44b is exposed in the spacing 72 and stays at the inspecting point;

Step 214: Enable the first and third image capturing elements 542, 562 to perform transverse linear shifting along the first and the second linear delivering mechanisms 541, 561 at the same time to execute continuous image-capturing to the upside and downside surfaces of the second side rim 44b for inspection; and Step 216: After the inspection, utilize the second conveyer 80 to keep on transporting the panel 40.

Wherein, during the inspection of short sides of the panel 40 in Steps 208, 214, the first and third image capturing elements 542, 562 transversely shifts along a direction of the spacing 72, whose moving routes are shown in FIG. 7 for example, in order to capture the images of the top and bottom surfaces of the second side rims 44a, 44b continuously. After the inspection of the short sides of the panel 40, the first and third image capturing elements 542, 562 move back to the inspection positions of long side for performing the inspection of long sides. In addition, in other embodiments of the present invention, in Steps 212, 214 of inspecting the back edge of the panel 40, the second side rim 44b, the second conveyer 80 may also move the panel 40 backward a short distance to make the second side rim 44b just stop at the inspecting point or locate in a preferable inspection location. Furthermore, at least an inspection parameter may be input in the panel inspection device 50 according to the size or specification of the panel 40 to be inspected in advance so as to set the motions or operations of the first, the second conveyers 70, 80 and the first, the second image-capturing units 54, 56 relative to and in accordance with the first and the second datum sensors 581, 582 in order to complete the above-mentioned inspection process of surface defect of panels.

In other embodiments of the present invention, the first and second image-capturing units 54, 56 may only have a first image capturing element 542 and a third image capturing element 562 for respectively inspecting defects of the top and bottom surfaces of the panel 40, without the second and fourth image capturing elements 543, 563. In addition, according to another embodiment of the present invention, the panel inspection device 50 may only include a single image-capturing unit, such as only include the first image-capturing unit 54, for inspecting the top surface of the panel 40 during transporting the panel 40 to the spacing 72. In this situation, a claw or other mechanism may be used to turn over the panel 40 in order to inspecting the bottom surface of the panel 40 with the same inspection process.

In addition, the first, second, third, and fourth image capturing elements 542, 543, 562, 563 may respectively have a CCD sensor, such as an area CCD or a line scan CCD. In accordance with the inspection method of the present invention panel, a good performance of image capturing can be obtained whether an area CCD or a linear scan CCD is adopted. As a result, in order to reduce equipment cost, area CCDs are preferably used as the sensor of the first, second, third, and fourth image capturing elements 542, 543, 562, 563.

According to the second embodiment of the present invention, only two datum sensors, two to four image capturing elements, and two linear delivering mechanisms (may have two linear motors) are needed to compose the main mechanism of the panel inspection device for inspecting edge defect of the panel only, and these components only need to be set near the spacing between two adjacent conveyers for performing the inspection of panel, so as to effectively decrease the occupation space of equipment. In addition, even though the panel to be inspected passes through the spacing between the conveyers slantingly, the panel inspection device of the present invention still can efficiently inspect the edge of the panel. Furthermore, in accordance with the coupled datum sensors and conveyers, the panel inspection method of the present invention controls the panel to be inspected to move backward or forward or to stop at the inspecting point, and utilizes the image capturing element capable of executing one-dimensional shifting to move transversely and capture the image of the panel at the same time. In contrast to the prior-art panel inspection device that has numerous apparatuses, such as at least two sets of linear delivering mechanisms and linear motors and a location-verifying image capturing element for assisting in locating the panel, and has to use a vacuum carrier and a claw to lift or lower, rotate, or turn over the panel, the panel inspection device of the present invention can effectively reduce equipment cost. Furthermore, in contrast to the prior-art inspection process, the panel inspection method of the present invention omits the steps of verifying the location of the panel mark, lifting and lowering the panel, rotating the panel, fastening the panel, and breaking vacuum, so as to reduce the total inspection time up to several seconds to effectively raise the production efficiency.

The inspection method and panel inspection device of present invention panel may be applied for any flat subjects, not limited to liquid crystal panels. For example, the panel inspection device and method according the present invention may also be utilized for inspecting OLED panel or other flat display panel. In contrast to the prior art, the panel inspection method and panel inspection device of the present invention only need simple components which occupy a little space and may be operated in coordination with any kind of in-line tool or equipments, by the way of performing the inspection of panel between adjacent equipments or conveyers. During the inspection of panels, the adjacent equipments or conveyers can still perform other fabrication processes such as sucking or fastening panel, transporting panels, inspecting display performance, eliminating static electricity, manually grabbing, or other processes. In addition, the panel inspection method of the present invention obviously reduces the total numbers of apparatuses and mechanisms in the prior-art technology, and an area CCD with low cost may be used as the image capturing element to replace the expensive line scan CCD in the prior art, so as to reduce equipment cost. Furthermore, even the sizes or specifications of panels are various during the inspection process, any modulation or manually adjusting of the mechanisms of the panel inspection device are not needed, which meet the requirements of economical efficiency and automation.

Those skilled in the art will readily observe that numerous modifications and alterations of the device and method may be made while retaining the teachings of the invention.

What is claimed is:

1. A panel inspection device for inspecting a panel that has at least a first side rim and at least a second side rim, the panel inspection device comprising:
    at least an image capturing element disposed above or below a spacing between a first conveyer and a second conveyer, wherein the first conveyer is used for transporting the panel to the second conveyer while the panel is transported along a direction substantially parallel to the first side rim;
    at least a datum sensor disposed in the spacing or on the first conveyer; and
    a first linear delivering mechanism disposed above or below the spacing, substantially along the direction of the spacing and corresponding to the first image capturing element so that the first image capturing element is capable of proceeding a linearly-shifting movement above or below the spacing along the first linear delivering mechanism;
    wherein when the second side rim of the panel passes through the datum sensor, the datum sensor starts the first image capturing element to execute an image-capturing motion to at least a portion of the panel after a predetermined time of the second side rim of the panel passes through the datum sensor.

2. The panel inspection device of claim 1, further comprising a panel positioning mechanism disposed on the first conveyer, used for enabling the panel to be transferred in a predetermined area on the first conveyer while the panel is being transferred to the second conveyer so that the first image capturing element is capable of directly capturing a characteristic or a mark of the panel without proceeding the linearly-shifting movement.

3. The panel inspection device of claim 1, further comprising a second image capturing element disposed above or below the spacing, wherein the panel has two first side rims, and when the panel is transported from the first conveyer to the second conveyer, the first and second image capturing elements are fixed at a respective position above or below the spacing for proceeding a continuous image-capturing motion to the first side rims of the panel.

4. The panel inspection device of claim 1, further comprising a second image capturing element disposed above or below the spacing, the second image capturing element is capable of executing a linearly-shifting movement along the spacing.

5. The panel inspection device of claim 1, wherein the panel has two first side rims and two second side rims, and the panel inspection device further comprises:

a second image capturing element disposed above the spacing, the first image capturing element, the second image capturing element, and the first linear delivering mechanism being defined as a first image capturing unit;

a second linear delivering mechanism disposed below the spacing in a way of parallel to the direction of the spacing;

a third image capturing element disposed below the spacing which is capable of executing a linearly-shifting movement, the third image capturing element being capable of performing a linearly-shifting movement along the second linear delivering mechanism below the spacing; and a fourth image capturing element disposed below the spacing, the third image capturing element, the fourth image capturing element, and the second linear delivering mechanism being defined as a second image capturing unit;

wherein when the panel is transported from the first conveyer to the second conveyer, the first image-capturing unit and the second image-capturing unit are capable of respectively executing continuously image-capturing motions to an upside and a downside of the first side rims.

6. The panel inspection device of claim 5, wherein the panel inspection device is capable of suspending the first conveyer from transporting the panel when one of the second side rim of the panel passes through the spacing or after a predetermined time of the second side rim passes through the datum sensor, enabling the first and the third image capturing elements to execute the linearly-shifting movements along the first and the second linear delivering mechanisms respectively so as to perform continuous image-capturing motions to an upside and a downside of the second side rims respectively while the panel is stopped, and controlling the first conveyer to continue transporting the panel to the second conveyer again after the first and the third image capturing elements finish the continuous image-capturing motions.

7. The panel inspection device of claim 5, wherein when the panel is transported out from the first conveyer and into the second conveyer, the panel inspection device suspends the second conveyer from transporting the panel so that one of the second side rim of the panel is exposed in the spacing and the first and the third image capturing elements execute the linearly-shift movements along the first and the second linear delivering mechanisms respectively to perform continuous image-capturing motion to an upside and a downside of the second side rim of the panel simultaneously.

8. The panel inspection device of claim 5, wherein the panel inspection device is used for performing an edge-defect inspection of the panel.

9. The panel inspection device of claim 1, wherein the first conveyer and the second conveyer are separate conveying device.

10. The panel inspection device of claim 1, wherein the first image capturing element has an area charge coupled device (CCD).

11. The panel inspection device of claim 1, further comprising a backlight source disposed below the spacing for providing a light source for the image-capturing motion.

12. The panel inspection device of claim 1, wherein the panel inspection device further comprises an image platform mounted at two sides of or on the first conveyer or the second conveyer, and the first linear delivering mechanism is disposed on the image platform.

13. A panel inspection method for inspecting a panel that has at least a first side rim and at least a second side rim, the panel inspection method comprising:

providing a first conveyer and a second conveyer adjacent to the first conveyer, a spacing being positioned between the first conveyer and the second conveyer, and the first conveyer being used for transporting the panel to the second conveyer substantially along a direction parallel to the first side rim;

providing a panel inspection device, comprising:
a first image capturing element disposed above or below the spacing;
a first linear delivering mechanism disposed above or below the spacing, the first linear delivering corresponding to the first image capturing element and being parallel to the direction of the spacing, and the first image capturing element being capable of executing a linearly-shifting movement above or below the spacing along the first linear delivering mechanism; and
at least a datum sensor disposed in the spacing or on the first conveyer;

utilizing the first conveyer to transport the panel to the second conveyer; and when the second side rim of the panel passes through the datum sensor, enabling the first image capturing element to execute an image-capturing motion to the panel after a predetermined time, wherein during the image-capturing motion, the first image capturing element is capable of executing the linearly-shifting movement along the first linear delivering mechanism to perform continuous image-capturing motions to the panel.

14. The panel inspection method of claim 13, further comprising setting an inspection parameter of the panel inspection device according to a specification or a size of the panel such that the first image capturing element executes the image-capturing motion at the predetermined time after the second side rim of the panel passes through the datum sensor according to the inspection parameter.

15. The panel inspection method of claim 13, wherein the panel comprises two first side rim, the panel inspection device further comprises a second image capturing element disposed above or below the spacing that is capable of executing a linearly-shifting movement along the spacing, and when the panel is transported from the first conveyer to the second conveyer, the first and the second image capturing elements are fixed above or below the spacing to execute continuous image-capturing motions to the first side rims respectively.

16. The panel inspection method of claim 13, wherein the first image capturing element is disposed above the spacing, the panel has two first side rims and two second side rims, and the panel inspection device further comprises:

a second image capturing element fixed above the spacing, the first image capturing element, the second image capturing element, and the first linear delivering mechanism being defined as a first image-capturing unit;

a third image capturing element disposed below the spacing which is capable of performing a linearly-shifting movement along the spacing; and a fourth image capturing element disposed below the spacing, the third image capturing element and the fourth image capturing element being defined as a second image-capturing unit;

the method further comprising enabling the first image-capturing unit and the second image-capturing to execute continuous image-capturing motions to upsides and downsides of the first side rims passing through the spacing respectively when the panel is transported from the first conveyer into the second conveyer.

17. The panel inspection method of claim 16, further comprising:
  during the first conveyer transporting the panel to the second conveyer, suspending the first conveyer from transporting the panel when one of the second side rims of the panel reaches the spacing;
  enabling the first and the third image capturing elements to respectively execute the linearly-shifting movements along the second side rim so as to perform continuous image-capturing motions to an upside and a downside of the second side rim respectively; and
  after performing the continuous image-capturing motions, continuously transporting the panel to the second conveyer.

18. The panel inspection method of claim 16, further comprising:
  after the first image-capturing unit and the second image-capturing unit execute the image-capturing motions to the first side rims respectively, suspending the first conveyer or the second conveyer from transporting the panel so that one of the second side rims of the panel is exposed in the spacing; and
  enabling the first and the third image capturing elements executing linearly-shifting motions along the second side rim so as to execute continuous image-capturing motions to an upside and a downside of the second side rim of the panel.

19. The panel inspection method of claim 16, wherein the panel inspection method is used for performing an edge-defect inspection of the panel.

20. The panel inspection method of claim 13, further comprising a backlight source disposed below the spacing for providing a light source for the image-capturing motion.

21. The panel inspection method of claim 13, further comprising providing a panel positioning mechanism for enabling the panel to be transported in a predetermined area on the first conveyer before the panel reaches the second conveyer such that the first image capturing element is capable of directly capturing a characteristic or a mark of the panel without executing the linearly-shifting movement.

22. The panel inspection method of claim 13, further comprising during inspecting a panel with different size, inputting an inspection parameter to enable the first image capturing element to linearly shift to an appropriate position such that the first image capturing element is capable of directly capturing a characteristic or a mark of the panel with different size.

23. The panel inspection method of claim 13, wherein the panel inspection device comprises two datum sensors disposed on the first conveyer and in the spacing respectively.

24. The panel inspection method of claim 13, wherein the panel inspection device comprises two datum sensors disposed on the second conveyer and in the spacing respectively.

25. The panel inspection method of claim 13, further comprising the following steps:
  providing an awaiting point and an inspecting point positioned on the first conveyer and the spacing respectively;
  when the panel passes through the awaiting point, decelerating the panel; and
  when the panel passes through the inspecting point, suspending the panel from being transported so as to allow the first image capturing element to execute the image-capturing motion.

* * * * *